United States Patent [19]

Dekker et al.

[11] Patent Number: 5,861,518

[45] Date of Patent: Jan. 19, 1999

[54] PHTHALIDE COMPOUNDS AND THEIR PRODUCTION PROCESS

[76] Inventors: Koenraad A. Dekker, 3-202-2-308 Kariyado-cho; Yuji Yamauchi, 1-98-3, Itayama-cho; Taisuke Inagaki, 18-203, Miyuki-cho, all of Handa-shi, Aichi-ken 475; Shinichi Sakemi, 1-1-2, Sakuragaoka, Taketoyo-cho, Chita-gun, Aichi-ken 470-23; Nakao Kojima, 3-153-1-501, Yashirodai, Meito-ku, Nagoya-shi, Aichi-ken 465, all of Japan

[21] Appl. No.: 836,203

[22] PCT Filed: Oct. 2, 1995

[86] PCT No.: PCT/IB96/00820

§ 371 Date: Oct. 31, 1997

§ 102(e) Date: Oct. 31, 1997

[87] PCT Pub. No.: WO96/16053

PCT Pub. Date: May 30, 1996

[30] Foreign Application Priority Data

Nov. 21, 1994 [JP] Japan .................................. 6-01962

[51] Int. Cl.$^6$ .......................... C07D 307/88; C12P 17/04; A61K 31/34

[52] U.S. Cl. ........................... 549/264; 549/304; 435/118; 435/126; 514/462; 514/469

[58] Field of Search ...................... 549/264, 304; 435/118, 126; 514/462, 469

[56] References Cited

FOREIGN PATENT DOCUMENTS

| 0282131 | 9/1988 | European Pat. Off. . |
| 2489328 | 3/1982 | France . |
| H06245793 | 9/1994 | Japan . |
| H07285862 | 10/1995 | Japan . |
| WO9203135 | 3/1992 | WIPO . |

OTHER PUBLICATIONS

Abstract of Japan Agri. Chem. 4Ep13, 1997.

A. Arnone et al. Chemical abstracts, vol. 112, No. 19, May 7, 1990 Columbus, Ohio abstract No. 175338z,.

A. Arnone et al. Phytochemistry, vol. 29, No. 2, 1990 pp. 613–616.

*Primary Examiner*—Bernard Dentz
*Attorney, Agent, or Firm*—Peter C. Richardson; Gregg C. Benson; Carl J. Goddard

[57] ABSTRACT

This invention provides processes for producing phthalide compounds which comprise cultivating Phanerochaete avelutina FERM BP-4787 and then isolating phthalide compounds from the fermentation broth.

5 Claims, No Drawings

PHTHALIDE COMPOUNDS AND THEIR PRODUCTION PROCESS

CROSS REFERENCE TO RELATED APPLICATIONS

This application is the National Stage of pending International Patent Application No. PCT/IB96/00820, filed on Oct. 02, 1995, entitled "Phthalide Compounds and their Production Process", which is a continuation in-part of International Patent Application No. PCT/JP94/01962, filed on Nov. 21, 1994, entitled "Phthalide Compounds and their Production Process", now abandoned.

1. Technical Field

This invention relates to novel phthalide compounds, and particularly to novel phthalide compounds produced by fermentation of a microorganism which has been deposited as FERM BP-4787. This invention also relates to processes for producing the phthalide compounds, and a pharmaceutical composition comprising the same, which is useful in the treatment of diseases, disorders and adverse conditions caused by *Helicobacter pylori* and is particularly useful in the treatment of gastroduodenal disorders, diseases and adverse conditions caused thereby.

2. Background Art

Gastric and duodenal ulcers affect a significant portion of the human population worldwide. Currently, the usual treatment for both gastric and duodenal ulcers involves treatment of the patient with histamine $H_2$ receptor antagonists ($H_2$ blockers). While generally effective in healing ulcers, ulcer relapse occures in up to 90% of patients within a year of discontinuing the $H_2$ blocker therapy. Thus, patients must continue the treatment for many years or risk a recurrence of the ulcer. It is now known that ulcer healing drugs such as colloidal bismuth subcitrate (CBS) are helicobactericidal and that such CBS is used in combination with $H_2$ blockers to treat ulcers. Additionally, CBS, an $H_2$ blocker and amoxicillin have been used in combination to treat ulcer patients.

*Helicobacter pylori* has been recently demonstrated to be a major causative agent in gastric and duodenal ulcers and other gastroduodenal disorders, diseases and adverse conditions. Thus, antibiotic therapy to eliminate *Helicobacter pylori* from the gastroduodenal tract would remove the root cause of said gastroduodenal disorders, diseases and adverse conditions and eliminate the need for an ulcer patient to continue long and costly treatment with $H_2$ blockers and the like. None of the foregoing treatments are capable of 100% eradication of *Helicobacter pylori*

Therefore, it would be desired to provide a compound having an excellent helicobactericidal activity.

The object of the present invention is to provide novel phthalide compounds having a excellent helicobactericidal activity and a pharmaceutical composition comprising the same. Another object of the present invention is to provide processes for producing the novel phthalide compounds.

BRIEF DISCLOSURE OF THE INVENTION

Accordingly, the present invention provides phthalide compounds of the formula:

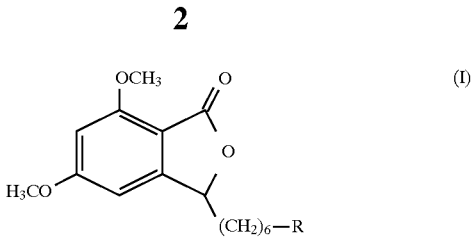

wherein R is a group of the formula:

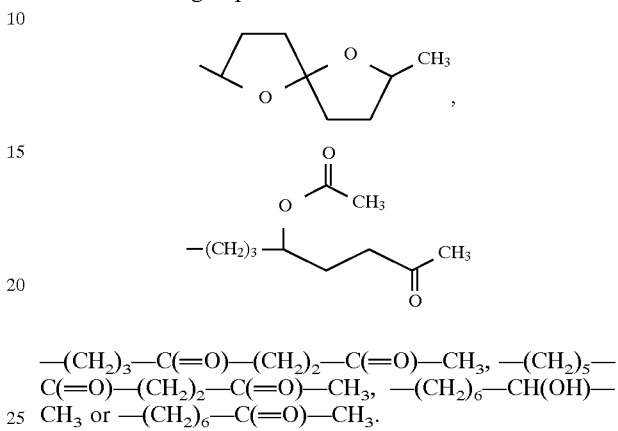

$-(CH_2)_3-C(=O)-(CH_2)_2-C(=O)-CH_3$, $-(CH_2)_5-C(=O)-(CH_2)_2-C(=O)-CH_3$, $-(CH_2)_6-CH(OH)-CH_3$ or $-(CH_2)_6-C(=O)-CH_3$.

Among the compounds of formula (I) of the present invention, prefer compound of formula (I) wherein R is:

Further, the present invention provides processes for producing the phthalide compounds of formula (I), which comprise cultivating a microorganism having identifying characteristics of FERM BP-4787, or a mutant or recombinant form thereof.

Also, the present invention provides a pharmaceutical composition for use in the treatment of *Helicobacter pylori*-induced disorders, diseases or adverse conditions caused thereby, such as gastroduodenal disorders including gastric ulcer, duodenal ulcer and gastric cancer, which comprises compounds of formula (I) and a pharmaceutically-acceptable carrier.

DETAILED DESCRIPTION OF THE INVENTION

The microorganism used in this invention is a strain of *Phanerochaete velutina* FPL 5362 which was obtained from the Forest Products Laboratory of the United States Department of Agriculture (Madison, Wis. It was deposited under the accession number FERM BP-4787 to National Institute of Bioscience and Human-Technology, Agency of Industrial Science and Technology (located at 1-3, Higashi 1-chome, Tsukuba, Ibaraki 305, Japan) under the Budapest Treaty on Aug. 25, 1994. The taxonomical properties of this strain have been reported by Burdsall, H. H., Jr. (Mycologia Memoir, 10, 133–139, 1985), describing that the strain is the basidiomycete *Panerochaete velutina*.

In this invention, a mutant or recombinant form of FERM BP-4787 having the ability to produce the phthalide compounds of formula (I) can be also used. The mutant or recombinant form may be obtained by spontaneous mutation, artificial mutation with ultraviolet radiation, or treatment with mutagen such as N-methyl-N'-nitro-N-nitrosoguanidine or ethyl methanesulfonate, or a cell technology method such as cell fusion, gene manipulation or the like, according to well-known methods.

According to the present invention, the phthalide compounds of formula (I) may be produced by aerobic fermentation of FERM BP-4787, or a mutant or recombinant form thereof, under conditions similar to those generally employed to produce bioactive compounds by fermentation.

FERM BP-4787, or a mutant or recombinant form thereof, is usually fermented on solid medium with an insoluble material and aqueous nutrient media. The amount of the insoluble material may range 10 to 50% (w/v). Suitable insoluble materials useful for fermentation include sand, cracked stone, wood chip and whole and broken grains, such as wheat bran, oatmeal, cracked corn, millet, etc. In this invention, cultivation of FERM BP-4787 to produce the novel phthalide compounds was preferably carried out using such insoluble materials and aqueous nutrient media at a temperature of 20° to 35° C. for 3 to 30 days. The pH of the medium may be adjusted in the range from 4.0 to 9.0, preferably from 5.0 to 7.5.

Nutrient media useful for fermentation include a source of assimilable carbon such as sugars, starches and glycerol; and a source of organic nitrogen such as casein, enzymatic digest of casein, soybean meal, cotton seed meal, peanut meal, wheat gluten, soy flour, meat extract and fish meal. A source of growth substances such as mineral salts, sodium chloride and calcium carbonate; and trace elements such as iron, magnesium, copper, zinc, cobalt and manganese may also be utilized with advantageous results.

FERM BP-4787, or a mutant or recombinant form thereof, can also be fermented under submerged aerobic conditions with agitation at a temperature of 15° to 40° C. for 3 to 25 days, which may be varied according to scale and fermentation conditions such as medium and temperature. FERM BP-4787 is preferably fermented to produce said phthalide compounds in aqueous nutrient media at a temperature of 20° to 35° C. for 3 to 25 days. The pH of the medium may be adjusted in the range from 4.0 to 9.0, preferably from 5.0 to 7.5. Nutrient media used for submerged aerobic conditions include those described above. If excessive foaming is encountered during fermentation, antifoam agent such as polypropylene glycols or silicones may be added to the fermentation medium.

The phthalide compounds thus produced may be isolated by standard techniques such as extraction and various chromatographic techniques. The phthalide compounds, CJ-12,954, CJ-13,014, CJ-13,015, CJ-13,102, CJ-13,103, CJ-13,104 and CJ-13,108 were isolated in a substantially pure form from the fermentation mixture, and identified by various spectroscopic techniques such as UV spectrophotometry, NMR and mass spectrometries. According to the analyses, these compounds are believed to have the following chemical formulas.

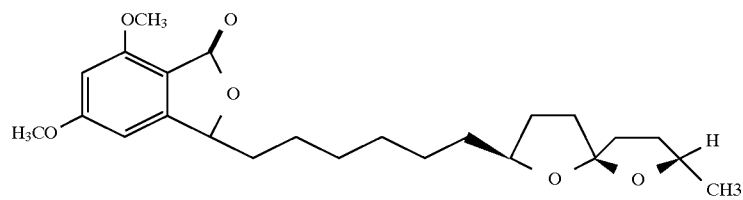

CJ-12954

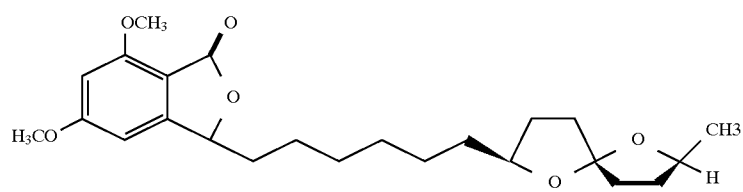

CJ-13014

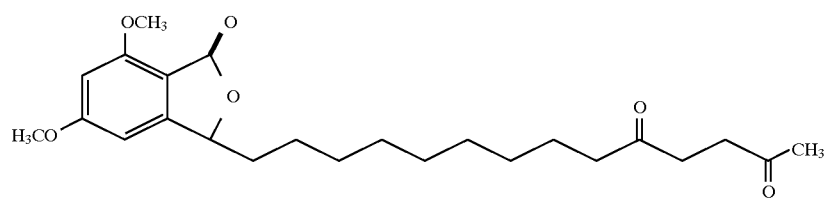

CJ-13015

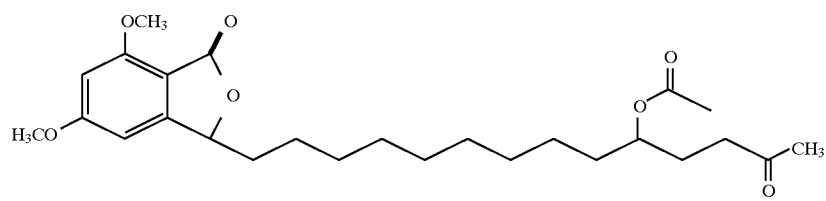

CJ-13102

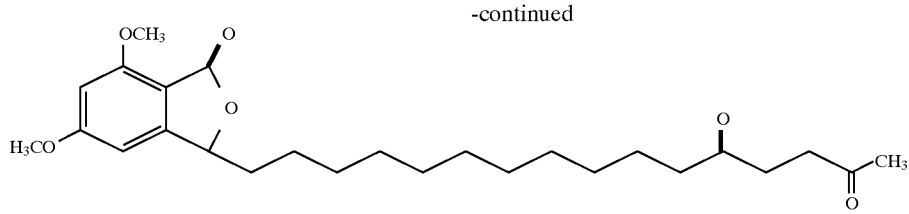

CJ-13103

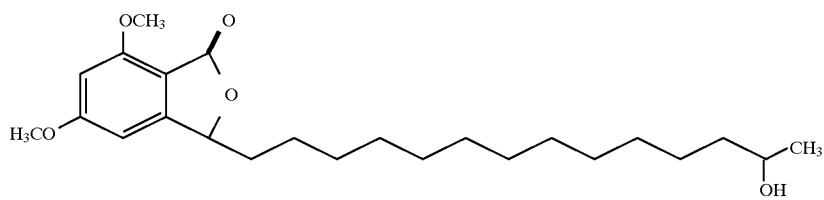

CJ-13104

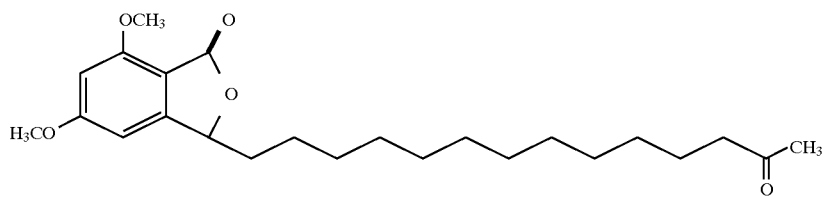

CJ-13108

The helicobactericidal activity of the phthalide compounds of this invention was determined by an agar plate dilution method using the paper disk (8 mm, ADVANTEC) and Brucella agar medium (BBL-Becton Dickinson Microbiology Systems). The phthalide compounds, CJ-12,954, CJ-13,014, CJ-13,015, CJ-13,102, CJ-13,103, CJ-13,104 and CJ-13,108 showed a helicobactericidal activity. Among these compounds, CJ-12,954 and CJ-13,014 showed especially high activity. When tested against other microorganisms such as *Bacillus stearothermophilus, Micrococcus luteus, Staphylococcus aureus* and *Pasteurella haemolytica* at the concentrations equivalent to those used in the above test, none of the phthalide compounds showed bactericidal activity against these microorganisms.

Accordingly, the phthalides compounds of formula (I) of the present invention are useful in the treatment of *Helicobacter pylori*-induced disorders, diseases or adverse conditions caused thereby, such as gastroduodenal disorders including gastric ulcer, duodenal ulcer and gastric cancer. For use as a helicobactericidal agent in a mammalian subject, especially a human subject, the phthalide compounds of formula (I) of the present invention can be administered either alone, or with an inert carrier in a pharmaceutical composition, according to standard pharmaceutical practice. The phthalide compounds of formula (I) of this invention may also be administered in combination with a suitable $H_2$ blocker such as ranitidine, cimetidine, famotidine or nizatinine, a proton pump inhibitor such as omeprazole, other antibiotic such as amoxicillin, or any combination thereof. If desired, CBS may be also added to the pharmaceutical composition. The compounds can be applied by parenteral or oral administration. The active ingredient may be compounded, for example, with the usual non-toxic, pharmaceutically-acceptable carriers for tablets, pellets, capsules, suppositories, solutions, emulsions, suspensions and other forms suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations. In addition, if needed, auxiliary, stabilizing and coloring agents and perfumes may be used. In general, the phthalide compounds of this invention are present in such dosage forms at concentration levels ranging 5 to 70% by weight, preferably 10 to 50% by weight.

The phthalide compounds of formula (I) of this invention can be used in mammalian subjects as helicobactericidal agents in dosages ranging from 0.01 to 20 mg/kg. The dosage to be used in a particular case will vary according to a number of factors such as the disease state or condition being treated, the potency of the individual compound being administered, the response of the particular subject and the route of administration. However, when a phthalide compound of formula (I) is used in a human patient to treat gastroduodenal disorders, the usual oral or parenteral dosage will be in the range from 0.5 to 250 mg and preferably 5 to 250 mg, one to four times per day.

EXAMPLES

The present invention is illustrated by the following examples. However, it should be understood that the invention is not limited to the specific details of these examples. Spectral and physico-chemical data were obtained by the following instruments: UV, JASCO Ubest-30; IR, Shimadzu IR-470; NMR, JEOL JNM-GX270 updated with a LSI-11/73 host computer, TH-5 tunable probe and version 1.6 software; and LREI- and HREI-MS, Hitachi M-80 with an M-003 data processing system. All NMR spectra were measured in $CDCl_3$ unless otherwise indicated and peak positions are expressed in parts per million (ppm) based on the internal standard of the $CHCl_3$ peak at 7.24 ppm. The peak shapes are denoted as follows: s (singlet), d (doublet), dd (doublet of doublet), t (triplet), q (quartet); m (multiplet), br (broad), brs (broad singlet) and sh (shoulder).

Example One

Cells from a 10- to 21-day-old petri dish of *Panerochaete velutina* (FERM BP-4787) grown on malt agar medium (malt extract 2.5% and agar 1.5%) were harvested and suspended in 2 ml sterile water. This suspension was used to inoculate 50-ml tubes containing 10 ml of Medium-1 (glucose 2%, malt extract 2%, yeast extract 1.8%, maltose 2.4% and agar 0.1%, pH 5.4~5.6). The tubes were incubated at 28° C. on a shaker at 250 rpm for 7 to 21 days.

Example Two

The cell suspension (2 ml) obtained by the method of Example One was used to inoculate two 500-ml flasks containing 100 ml of Medium-1. The flasks were incubated at 28° C. for 7 days. These flasks were used to inoculate 7.5 ml into fifteen 500-ml flasks containing 150 ml of Medium-1. These seed cultures in the 15 flasks were used to inoculate 100 ml into fifteen 6-1 fermentation vessels containing 0.5 l of Medium-2 (glucose 1%, glycerol 3%, peptone 0.5%, NaCl 0.2%, agar 0.1% and pH 6.9~7.1) and 200 g oatmeal. Incubation was carried out at 28° C. for 14 to 28 days.

Example Three

According to the method of Example Two, fermentation was carried out, except that the seed cultures in 12 shake flasks were used to inoculate 100 ml into twelve 6l fermentation vessels containing 0.5 or 0.75l of Medium-1 and 300 g wheat bran. Incubation was carried out at 28° C. for 14 to 28 days.

Example Four
Isolation of Phthalide Compounds

To each of the twelve 6 l fermentation vessels of Example Three, 2 l of ethanol was added. The combined broth was filtered, the filtrate was concentrated to aqueous solution (6 l), and extracted three times with 5 l of ethyl acetate. The extract was dried over anhydrous $Na_2SO_4$ and evaporated to afford an oily residue (84.4 g). The oily residue was loaded on a silica gel column and compounds were eluted with ethyl acetate-n-hexane (1:3) (3 ), then ethyl acetate-n-hexane (1:1) (3). Fractions showing activity were applied separately to a Sephadex LH-20 (Pharmacia trademark) column and eluted with methanol. Fractions containing phthalide compounds were further applied to a Chemcosorb 5ODS-UH (Chemco trademark) column (20×250 mm) and eluted with acetonitrile-water (13:7) for 120 min at a flow rate of 10 ml/min. The detection was made by UV absorbance at 230 nm.

The eluted peaks showing activity were collected to yield the compounds CJ-12,954 (15.2 mg), CJ-13,014 (14.3 mg), CJ-13,015 (7.8 mg), CJ-13,102 (21.1 mg), CJ-13,103 (4 mg), (CJ-13,104 (14.1 mg) and CJ-13,108 (54 mg). The seven compounds were separated by HPLC using a YMC-pack ODS AM-302 (Yamamura trademark) (150×4.6 mm column) and eluted with methanol-water (3:1) for 30 min at a flow rate of 1 ml/min at 40° C. The retention times (min) of the separated compounds were 10.7 (CJ-12,954), 11.4 (CJ-13,014), 22.1 (CJ-13,015), 11.0 (CJ-13,102), 11.8 (CJ-13,103), 24.4 (CJ-13,104) and 20.9 (CJ-13,108).

Characterization

The physicochemical properties of CJ-12,954, CJ-13,014, CJ-13,015, CJ-13,102, CJ-13,103, CJ-13,104 and CJ-13,108 are as follows.

CJ-12,954

Colorless glass; $[\alpha]_D^{24}$+6.0° (c 0.07, $CHCl_3$); HREI-MS (m/z) obs. 418.2355 (calcd. for $C_{24}H_{34}O_6$, 418.2354); UV $\lambda_{max}$ (MeOH, nm) 217.4 ($\epsilon$30,000), 257.6 ($\epsilon$14,000) and 290.6 ($\epsilon$5,000); IR (KBr, $cm^{-1}$) 2930, 1754, 1606, 1489, 1457, 1433, 1333, 1214, 1155, 1105, 1051, 1027, 985, 856, 836 and 688; LREI-MS (m/z) 418 (2.7%, rel. int.), 403 (1.0), 400 (1.2), 385 (2.4), 374 (4.9), 363 (4.8), 361 (16.1), 320 (33.1), 318 (7.8), 307 (6.5), 303 (3.5), 279 (5.3), 278 (8.8), 207 (22.8), 194 (29.6), 193 (80.6), 177 (6.1), 165 (12.2), 141 (100), 112 (21.3), 85 (68.1), 55 (29.1) and 41 (24.5); $^1$H NMR δ6.39 (1H, brs), 6.38 (1H, brs), 5.27 (1H, dd, J=8.1, 3.7 Hz), 4.08 (1H, m), 3.93 (3H, s), 3.90 (1H, m), 3.87 (3H, s), 2.05~1.80 (7H, m) 1.80~1.55 (4H, m), 1.55~1.20 (9H, m) and 1.27 (3H, d, J=6.2 Hz); $^{13}$C NMR δ168.5 (s), 166.6 (s), 159.6 (s), 155.2 (s), 114.2 (s), 106.9 (s), 98.6 (d), 97.3 (d), 79.9 (d×2), 75.8 (d), 56.0 (q), 55.9 (q), 37.3 (t), 36.5 (t), 36.1 (t), 34.8 (t), 32.6 (t), 30.7 (t), 29.4 (t), 29.3 (t), 25.9 (t), 24.6 (t) and 23.0 (q).

CJ-13,014

Colorless glass; $[\alpha]_D^{24}$+71.2° (c 0.11, $CHCl_3$); HREI-MS (m/z) obs. 418.2355 (calcd. for $C_{24}H_{34}O_6$, 418.2354); UV $\lambda_{max}$ (MeOH, nm) 217.0 ($\epsilon$34,000), 257.8 ($\epsilon$16,000) and 290.4 ($\epsilon$5,6000); IR (KBr, $cm^{-1}$) 2930, 1753, 1607, 1489, 1457, 1432 1333, 1214, 1156, 1100, 1050, 1027, 916, 894, 865, 835 and 690; LREI-MS (m/z) 418 (3.7%, rel. int.), 403 (1.2), 400 (1.7), 385 (2.4), 374 (5.1), 363 (6.2) 361 (35.2), 360 (5.7), 345 (1.1), 320 (19.7), 318 (8.6), 307 (8.6), 303 (4.2), 279 (4.4), 278 (7.9), 207 (24.0), 194 (28.0), 193 (79.9), 191 (7.1), 177 (5.9), 165 (11.4), 141 (100), 135 (7.5), 123 (4.9), 122 (6.4), 112 (24.4), 85 (54.4), 67 (7.8), 57 (10.6), 56 (15.8) and 55 (26.0); $^1$H NMR δ6.39 (1H, brs), 6.38 (1H, brs), 5.27 (1H, dd, J=8.1, 3.7 Hz), 4.16 (1H, m), 4.01 (1H, m), 3.93 (3H, s), 3.87 (3H, s), 2.15~1.90 (7H, m), 1.65 (1H, m), 1.55~1.35 (6H, m), 1.35~1.25 (6H, m) and 1.19 (3H, d, J=6.2 Hz); $^{13}$C NMR δ168.5 (s), 166.6 (s), 159.6 (s), 155.2 (s), 114.7 (s), 106.9 (s), 98.6 (d), 97.3 (d), 79.9 (d), 78.1 (d), 74.0 (d), 56.0 (q), 55.9 (q), 35.7 (t), 35.6 (t×2), 34.8 (t), 32.2 (t), 30.2 (t), 29.4 (t), 29.3 (t), 25.7 (t), 24.6 (t) and 21.1 (q).

CJ-13,015

Colorless glass; $[\alpha]_D^{25}$+25.6° (c 0.22, $CHCl_3$); HREI-MS (m/z) obs. 418.2358 (calcd. for $C_{24}H_{34}O_6$, 418.2354); UV $\lambda_{max}$ (MeOH, nm) 217.4 ($\epsilon$32,000), 257.6 ($\epsilon$15,000) and 290.4 ($\epsilon$5,800); IR (KBr, $cm^{-1}$) 2920, 2850, 1757, 1697, 1612, 1599, 1493, 1465, 1426, 1412, 1350 (sh), 1333, 1220, 1197, 1160, 1096, 1050, 1023, 835 and 689; LREI-MS (m/z) 418 (10.3%, rel. int.), 400 (11.8), 375 (3.8), 347 (18.2), 320 (11.4), 305 (70.0), 207 (36.8), 194 (28.7), 193 (100), 165 (13.7), 99 (19.3) and 43 (32.3); $^1$H NMR δ66.39 (1H, brs), 6.38 (1H, brs), 5.27 (1H, dd, J=8.1, 3.7 Hz), 3.93 (3H, s), 3.87 (3H, s), 2.67 (4H, m), 2.42 (2H, t, J=7.5 Hz), 2.17 (3H, s), 1.95 (1H, m), 1.66 (1H, m), 1.54 (2H, m), 1.42 (2H, m) and 1.24 (10H, brs); $^{13}$C NMR δ209.7 (s), 207.4 (s), 168.6 (s), 166.6 (s), 159.5 (s), 155.2 (s), 106.7 (s), 98.6 (d), 97.3 (d), 80.0 (d), 55.9 (q×2), 42.7 (t), 36.8 (t), 36.0 (t), 34.8 (t), 29.9 (q), 29.2 (t×4), 29.1 (t), 24.6 (t) and 23.7 (t).

CJ-13,102

Colorless glass; $[\alpha]_D^{25}$+26.8° (c 0.81, $CHCl_3$); HREI-MS (m/z) obs. 462.2620 (calcd. for $C_{26}H_{38}O_7$, 462.2616); UV $\lambda_{max}$ (MeOH, nm) 217.2 ($\epsilon$24,000), 257.4 ($\epsilon$11,000) and 290.4 ($\epsilon$4,000); IR (KBr, $cm^{-1}$) 2925, 2850, 1754, 1732, 1606, 1489, 1460, 1430, 1356, 1334, 1239, 1217, 1157, 1102, 1052, 1027 and 835; LREI-MS (m/z) 462 (5.5%, rel. int.), 402 (91.5), 363 (47.9), 345 (43.2), 207 (39.0), 194 (29.7), 193 (100), 165 (13.3) and 43 (66.0); $^1$H NMR δ6.38 (2H, brs), 5.26 (1H, dd, J=7.7, 3.7 Hz), 4.81 (1H, m), 3.91 (3H, s), 3.86 (3H, s), 2.42 (2H, t, J=7.5 Hz), 2.11 (3H, s), 2.00 (3H, s), 2.00~1.55 (4H, m), 1.55~1.30 (4H, m) and 1.21 (12H, brs); $^{13}$C NMR δ208.0 (s), 170.9 (s), 168.5 (s), 166.6 (s), 159.6 (s), 155.2 (s), 106.9 (s), 98.6 (d), 97.4 (d), 79.9 (d), 73.5 (d), 55.9 (q×2), 39.5 (t), 34.8 (t), 34.2 (t), 29.9 (q), 29.3 (t×4), 29.2 (t), 27.9 (t), 25.2 (t), 24.6 (t) and 21.1 (q).

CJ-13,103

Colorless glass; $[\alpha]_D^{25}$+26.0° (c 0.10, $CHCl_3$); HREI-MS (m/z) obs. 446.2665 (calcd. for $C_{26}H_{38}O_6$, 446.2666); UV $\lambda_{max}$ (MeOH, nm) 216.8 ($\epsilon$26,000), 257.4 ($\epsilon$12,000) and 290.0 ($\epsilon$4,600); IR (KBr, cm$^{-1}$) 2920, 2845, 1759, 1699, 1612, 1599, 1492, 1463, 1426, 1412, 1356, 1332, 1220, 1195, 1160, 1095, 1047, 1024, 834 and 690; LREI-MS (m/z) 446 (18.5%, rel. int.), 428 (19.8), 403 (6.2), 375 (21.2), 348 (13.4), 333 (100), 207 (32.0), 194 (25.1), 193 (69.6), 165 (8.8), 99 (13.7), 71 (9.7), 55 (109) and 43 (23.4); $^1$H NMR $\delta$6.39 (1H, brs), 6.38 (1H, brs), 5.27 (1H, dd, J=7.7, 3.7 Hz), 3.93 (3H, s), 3.87 (3H, s), 2.66 (4H, m), 2.42 (2H, t, J=7.5 Hz), 2.16 (3H, s), 1.94 (1H, m), 1.64 (1H, m), 1.52 (2H, m), 1.41 (2H, m) and 1.22 (14H, brs).

CJ-13,104

Colorless glass; $[\alpha]_D^{25}$+36.1° (c 0.41, CHCl$_3$); HREI-MS (m/z) obs. 406.2713 (calcd. for C$_{24}$H$_{38}$O$_5$, 406.2716); UV $\lambda_{max}$ (MeOH, nm) 216.4 ($\epsilon$27,000), 257.6 ($\epsilon$12,000) and 289.4 ($\epsilon$4,400); IR (KBr, cm-1) 2915, 2845, 1755, 1736, 1611, 1599, 1493, 1462, 1426, 1336, 1220, 1197, 1160, 1097, 1052, 1026, 983, 936, 835 and 690; LREI-MS (m/z) 406 (1.2%, rel. int.), 388 (21.2), 362 (93.1), 207 (53.9), 194 (35.6), 193 (100), 165 (13.5), 55 (16.5), 45 (39.6) and 41 (14.9) $^1$H NMR $\delta$6.38 (2H, m), 5.26 (1H, dd, J=7.7, 3.7 Hz), 3.92 (3H, s), 3.86 (3H, s), 3.77 (1H, m), 2.20 (1H, br), 1.95 (1H, m), 1.65 (1H, m), 1.50~1.35 (4H, m), 1.22 (18H, brs) and 1.16 (3H, d, J=6.2 Hz); $^{13}$C NMR $\delta$168.5 (s), 166.6 (s), 159.6 (s), 155.2 (s), 106.9 (s), 98.6 (d), 97.4 (d), 79.9 (d), 68.2 (d), 56.0 (q), 55.9 (q), 39.3 (t), 34.8 (t), 29.6 (t×5), 29.5 (t), 29.4 (t), 29.3 (t), 25.7 (t), 24.6 (t) and 23.4 (q).

CJ-13,108

Colorless glass; $[\alpha]_D^{25}$+44.8° (c 0.50, CHCl$_3$); HREI-MS (m/z) obs. 404.2557 (calcd. for C$_{24}$H$_{36}$O$_5$, 404.4559); UV $\lambda_{max}$ (MeOH, nm) 217.4 ($\epsilon$30,000), 257.2 ($\epsilon$14,000) and 290.2 ($\epsilon$5,200); IR (KBr, cm$^{-1}$) 2915, 2845, 1756, 1707, 1611, 1600, 1492, 1464, 1425, 1355, 1333, 1219, 1195, 1159, 1099, 1050, 1023, 995, 974, 833 and 690; LREI-MS (m/z) 404 (58.7%, rel. int.), 347 (81.5), 207 (43.8), 194 (31.1), 193 (100), 165 (13.4), 58 (15.5) and 43 (42.8); $^1$H NMR $\delta$6.36 (2H, brs), 5.23 (1H, dd, J=7.7, 3.7 Hz), 3.89 (3H, s), 3.84 (3H, s), 2.36 (2H, t, J=7.3 Hz), 2.07 (3H, s), 1.91 (1H, m), 1.64 (1H, m), 1.50 (2H, m), 1.38 (2H, m) and 1.18 (16H, brs); $^{13}$C NMR $\delta$209.3 (s), 168.4 (s), 166.6 (s), 159.5 (s), 155.1 (s), 106.8 (s), 98.5 (d), 97.4 (d), 79.9 (d), 55.9 (q), 55.8 (q), 43.7 (t), 34.7 (t), 29.7 (q), 29.4 (t×3), 29.3 (t×3), 29.2 (t), 29.0 (t), 24.5 (t) and 23.7 (t).

We claim:

1. A phthalide compound of the formula:

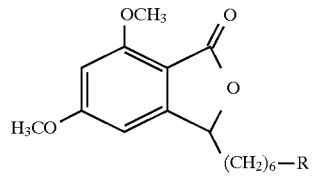

wherein R is a group of the formula:

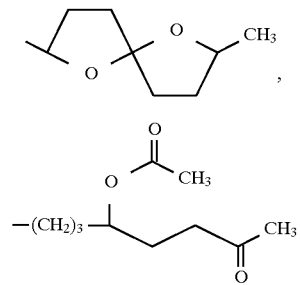

—(CH$_2$)$_3$—C(=O)—(CH$_2$)$_2$—C(=O)—CH$_3$, —(CH$_2$)$_5$—C(=O)—(CH$_2$)$_2$—C(=O)—CH$_3$, —(CH$_2$)$_6$—CH(OH)—CH$_3$ or —(CH$_2$)$_6$—C(=O)—CH$_3$.

2. A phthalide compound according to claim 1, wherein R is:

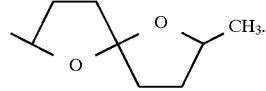

3. A process for producing phthalide compounds according to claim 1, which comprises cultivating a microorganism having the identifying characteristics of *Panerochaete velutina* FERM BP-4787, or a mutant or recombinant form thereof.

4. A process according to claim 3, which further comprises the subsequent step of isolating said phthalide compounds from the fermentation broth.

5. A pharmaceutical composition for use in the treatment of *Helicobacter pylori* induced disorders, diseases or adverse conditions caused thereby, which comprises a compound according to claim 1 and a pharmaceutically-acceptable carrier.

* * * * *